United States Patent [19]

DeSimone

[11] Patent Number: 5,079,023
[45] Date of Patent: Jan. 7, 1992

[54] FOODSTUFFS CONTAINING ALDEHYDE GENERATORS

[75] Inventor: Robert S. DeSimone, Oakland, N.J.

[73] Assignee: Hercules Incorporated, Wilmington, Del.

[21] Appl. No.: 380,830

[22] Filed: Jul. 17, 1989

Related U.S. Application Data

[60] Division of Ser. No. 71,550, Jul. 7, 1987, abandoned, which is a continuation of Ser. No. 714,065, Mar. 20, 1985, abandoned, which is a continuation of Ser. No. 571,633, Jan. 16, 1984, abandoned, which is a continuation of Ser. No. 372,425, Apr. 27, 1982, abandoned, which is a continuation of Ser. No. 197,398, Oct. 16, 1980, abandoned, which is a continuation-in-part of Ser. No. 893,907, Apr. 5, 1978, Pat. No. 4,280,011, which is a continuation-in-part of Ser. No. 761,183, Jan. 21, 1977, abandoned.

[51] Int. Cl.$^5$ .............................................. A23L 1/226
[52] U.S. Cl. .................................. 426/534; 426/536; 426/538; 568/603
[58] Field of Search ................ 568/603; 426/534, 536, 426/538

[56] References Cited

U.S. PATENT DOCUMENTS

| | | | |
|---|---|---|---|
| 2,000,252 | 5/1935 | Reppe et al. | 568/594 |
| 3,829,504 | 8/1974 | Hall et al. | 568/592 |
| 3,857,964 | 12/1974 | Yolles | 426/534 |
| 3,920,755 | 11/1975 | Schreiber et al. | 426/534 X |
| 3,922,309 | 11/1975 | Schreiber et al. | 426/534 X |
| 3,922,351 | 11/1975 | Dietrich et al. | 426/534 X |
| 4,280,011 | 7/1981 | DeSimone | 426/536 X |

OTHER PUBLICATIONS

Perfumer & Flavorist, DeSimone and Byrne, pp. 15-26., Dec. 1986/Jan. 1987.

*Primary Examiner*—Joseph Golian
*Attorney, Agent, or Firm*—David Edwards; Dale Lovercheck

[57] ABSTRACT

The use of acetals as aldehyde generators in foodstuff applications is disclosed.

24 Claims, 3 Drawing Sheets

FOODSTUFFS CONTAINING ALDEHYDE GENERATORS

This is a divisional of application Ser. No. 071,550, filed July 7, 1987, now abandoned, which is a continuation of U.S. Ser. No. 714,065, filed Mar. 20, 1985, now abandoned, which is a continuation of U.S. Ser. No. 571,633, filed Jan. 16, 1984, now abandoned, which is a continuation of U.S. Ser. No. 372,425, filed Apr. 27, 1982, now abandoned, which is a continuation of U.S. Ser. No. 197,398, filed Oct. 16, 1980, now abandoned, which is a continuation-in-part of U.S. Ser. No. 893,907, filed Apr. 5, 1978, now U.S. Pat. No. 4,280,011, which is a continuation-in-part of U.S. Ser. No. 761,183, filed Jan. 21, 1977, now abandoned.

This invention relates to a novel method of fixing aldehydes by means of certain acetals which act as generators responding to the conditions of use in a food product to yield the regenerated aldehyde. This invention also relates to processes for making the above-mentioned aldehyde generating acetals and to their use in flavors to generate the desired aldehydes.

It is well known that both acetaldehyde and propionaldehyde occur in a wide variety of fresh and prepared foodstuffs, such as fruits, meat, dairy products, baked goods and vegetables. Acetaldehyde has been found particularly important in contributing to the flavor impact and "fresh" effect of certain foodstuffs, especially of the citrus fruit and red berry types. As such, it is indispensable in compounding artificial flavors where the "fresh effect" is needed. The same can be said of propionaldehyde, which also contributes to the flavor of a wide range of fruit and food types.

Acetaldehyde is found in many fruits, such as apple, arctic bramble, banana, cherry and morello, citrus fruits, cranberry and bilberry, currants, grape, olive, passionfruit, peach, plum, strawberry and raspberry. It is found in many vegetables, such as carrot, celery, cucumber, mushroom, onion, garlic, peas, potato, and tomato. It is found in the spice ginger. It is found in bread products, such as white bread, crisp bread, and bread pre-ferment. It is found in milk products, such as blue cheese, swiss cheese, and milk and milk products in general. It is found in alcoholic beverages, such as beer, Bantoo beer, plum brandy, whiskey, apple wine, and wine. It is found in fish and meat, such as caviar, fish, cooked chicken, heated beef, heated lamb, and heated pork. It is found in miscellaneous foods, such as coffee, tea, peanuts (roasted), potato chips, soybeans, and eggs.

Other aliphatic aldehydes, such as butyraldehyde, octylaldehyde, and the like, varying in carbon number from $C_4$ to about $C_{12}$, are known for giving impact and special flavor effects in a wide variety of flavors corresponding to their occurrence in nature in a wide variety of foodstuffs and these other aldehydes can also be fixed according to the principles of this invention. For example, butyraldehyde occurs in apple, strawberry, milk, fish, beef, pork, beer, banana, cranberry, grape, peach, onion, potato, ginger, bread and blue cheese; 2-methyl propanal is found in potato, tomato, bread, blue cheese, milk, cacao, egg, fish, beef, pork and sherry; 2-methyl butanal is found in cacao, egg, fish, beef, beer, currant and olive; 3-methyl-butyraldehyde occurs in cacao, fish, chicken, beef, beer, peanut, currant, olive, peach and mushroom; valeraldehyde occurs in milk, tea, fish, chicken, beef, pork, beer, cranberry, currant, grape, olive, mushroom, onion and potato; 2-ethoxy propanal occurs in rum, as does 3-ethoxy propanal; 3-methyl pentanal occurs in beer; 2-methyl pentanal occurs in onion; 2-ethyl butanal occurs in citrus and bread; hexanal occurs in banana, citrus, soy beans, milk, fish, chicken, beef, lamb, tea, cranberry, grape, olive, melon, peach, cucumber, mushroom, onion, potato and tobacco; heptaldehyde is found in citrus, cranberry, currant, grape, olive, peach and bread. Octaldehyde is found in bread, carrot, olive and citrus; nonylaldehyde is found in banana, citrus, cranberry, milk, fish, beef, beer, tea, chicken, currant, melon, olive, carrot, ginger and bread; decanal occurs in bread, ginger, milk, fish, cacao, beer, cucumber, grape and citrus; undecylaldehyde is found in citrus, milk, fish, beef and cucumber; while dodecanal is found in milk, fish, beef, citrus, grape and cucumber; cis-6-nonenal is found in melon and cucumber; and phenyl acetaldehyde is found in peach, beans, mushroom, mint and blue cheese.

Much effort has been expended in the last two decades, as attested by patent literature on the subject, to provide a stable "fixed" form of acetaldehyde which would release only under the desired conditions of use and not before. The main reason for this difficulty in "fixing" acetaldehyde lies in its physical characteristics of being a gas at room temperature (21° C.) under normal ambient conditions, being miscible with water, and having a high degree of chemical reactivity and instability. Its chemical instability is exemplified by its tendency to polymerize or form paraldehyde and metaldehyde, oxidize to acetic acid, or combine chemically with itself and other materials in the presence of an acid or base.

To accomplish fixation of acetaldehyde, workers have sought to entrap it in crystal defect or clathrate inclusion complexes of a variety of types, including those based on oligosaccharides or monosaccharides. The inclusion complex releases acetaldehyde under the conditions of use, such as when a dry beverage powder is dissolved in water. The drawback to this method, in general, is that only a small amount of acetaldehyde is fixed in stable form by these methods giving a large ratio of inclusion matrix to aldehyde and making it quite expensive to use the aldehyde in this form. For example, Dame et al in U.S. Pat. No. 3,314,803 present a method for encapsulating acetaldehyde in a mannitol matrix. An initial acetaldehyde entrapment of 2 to 10% is realized upon spray drying the mannitol-acetaldehyde mixture. When exposed to ambient conditions in the open, however, acetaldehyde is rapidly lost to the atmosphere and, within a few days, the acetaldehyde concentration is reduced to a maximum long-term stable fix of between 1 and 2.5%. This loss of acetaldehyde from the matrix is even observed upon incorporation of the encapsulate in a food base, such as a dry beverage powder contained in a package, especially in the presence of small amounts of water or water vapor, either of which may be present in the food product base itself or entrained during the normal packaging operations.

Other examples of polysaccharide inclusion matrices in the patent literature include a carbohydrate complex in U.S. Pat. No. 3,625,709 to Mitchell, the use of arabinogalactan by Glicksman and Schachat in U.S. Pat. No. 3,264,114, and the use of lactose by Knapp in U.S. Pat. No. 3,736,149. All of the latter methods suffer from the disadvantage of a low degree of acetaldehyde fixation. Moreover, they exhibit instability in the presence of small amounts of water or water vapor, which would be incurred upon storage in a non-hermetically sealed package, which is sufficiently permeable to allow atmospheric moisture to enter, or to the exposure incurred during normal processing and packaging operations.

Earle, in U.S. Pat. No. 3,767,430, describes a method of "fixing" acetaldehyde in a sucrose crystal matrix but the amount of acetaldehyde is less than 0.1% and generally about 0.001 to 0.05%.

The second method of "fixing" acetaldehyde is that of chemical derivatization, which must satisfy several, often conflicting requirements, including that of chemical inertness and stability under the usual storage conditions, quick release of aldehyde upon mixing or preparing the food product for use, and the property of not interfering with the aroma or taste of the desired flavor. To satisfy the latter requirement the derivative and its conversion products, other than the target aldehyde, should be relatively odorless and tasteless.

Many attempts to provide suitable chemical derivatives for generating acetaldehyde are evinced in the patent literature. A variety of aldehyde derivatives have been proposed for generating acetaldehyde, including carbamates, carbonates, ureides, ethylidene compounds (U.S. Pat. No. 2,305,620) and certain acetals (U.S. Pat. Nos. 3,829,504 and 3,857,964). All the aforementioned derivatives suffer from at least some of the disadvantages of producing off-tastes, being toxic, or being too stable to release at an appropriate rate in the desired foodstuff or in having their own taste and odor effect.

Use of well-known acetals of acetaldehyde, propionaldehyde, and other aliphatic aldehydes, up to about dodecylaldehyde, derived from monohydric alcohols, such as dimethyl, diethyl and dihexyl acetals, is precluded by the taste of the acetal itself, which is usually unacceptably different from that of the parent aldehyde, and thus interferes with the balance of the desired flavor, especially in the case of the acetals of the $C_1$ to about $C_8$ aldehydes. Moreover, use of alcohols to make such acetals is limited to those aliphatic alcohols having 1 to 5 carbon atoms, cyclohexanol or benzyl, since aliphatic alcohols of $C_6$ and higher, up to about $C_{12}$, lend their own flavor and also distort the intended flavor.

It is the object of this invention to provide acetals which fulfill the major requirements of stability and of "fixing" aldehydes in flavors and flavored food bases, and of providing a quick-release effect under the conditions of intended use. These acetals also do not interfere with the desired flavor, are stable to moisture, heat, and oxidation under normal conditions of storage, are capable of being incorporated into a dry flavor and remaining stable, and provide a higher percentage of stable, fixed acetaldehyde in a dry flavor or flavor base than has heretofore been found possible.

The acetals of the invention consist of structural types A and B, where the active portion of the molecule is a linear acetal:

where R is a 2 to 6 (i.e., 2, 3, 4, 5 or 6) carbon atom multivalent hydrocarbon radical; n is 1, 2, 3, 4, 5 or 6 an integer equal to or less than the valence of R, but at least one, and in the case where n is less than the valence of R, the remaining valences of R are satisfied by functional groups selected from the class consisting of alkoxy, carbonyl oxygen, hydroxy, acyloxy, acyl, carbalkoxy, carboxyl, acetal, ketal, alkylaromatic, dioxolane, or dioxane groups or hydrocarbon radicals containing such groups consistent with the formation of a parent compound which itself has a low taste and odor and which yields only hydrolysis products having low taste and odor; where $R_1$, the aldehyde residue, is a radical selected from the class consisting of:

(a) 1 to 14 (i.e. 1, 2, 3, 4, 5, 6, 7, 8, 9, 10, 11, 12, 13 or 14) carbon hydrocarbon radicals which can be branched or straight chain alkyl or alkenyl; cycloalkyl or cycloalkenyl; phenyl or benzyl; and (b) furyl where $R_2$ is (a) an aliphatic or cycloaliphatic hydrocarbon moiety of up to 7 (i.e. 1, 2, 3, 4, 5, 6 or 7) carbon atoms corresponding to an alcohol which does not, itself, have a strong taste or odor, such as benzyl, methyl, ethyl, propyl, t-butyl, prenyl or butenyl, but preferably methyl or ethyl, or a benzyl group;

(b) A $C_2$ to $C_{18}$ aliphatic, cycloaliphatic or monocyclic aromatic acyl group or an oxygenated derivative thereof which, upon hydrolysis of the acetal linkage, yields an acid which will not distort the desired flavor; or (c) a 5 or 6 carbon cycloaliphatic ether; and where $R_3$ is (a) a cycloaliphatic ether, dioxane, or dioxolane group;

(b) a hydrocarbon radical corresponding to $R_2$ with the further limitation that the total carbon number of $R_2$ and $R_3$ combined is between 9 and 14; or (c) a radical of the general formula:

where $R_4$ and $R_5$ are hydrogen or the same or different alkyl groups, and $R_6$ is a functional group selected from the class consisting of phenyl, alkyl aromatic, phenoxy, alkoxy, dioxolane or metadioxane groups, or a hydrocarbon moiety containing such a group, consistent with the formation of a parent compound which itself has a low taste and odor, and which yields only hydrolysis products having low taste and odor.

Figure 1:
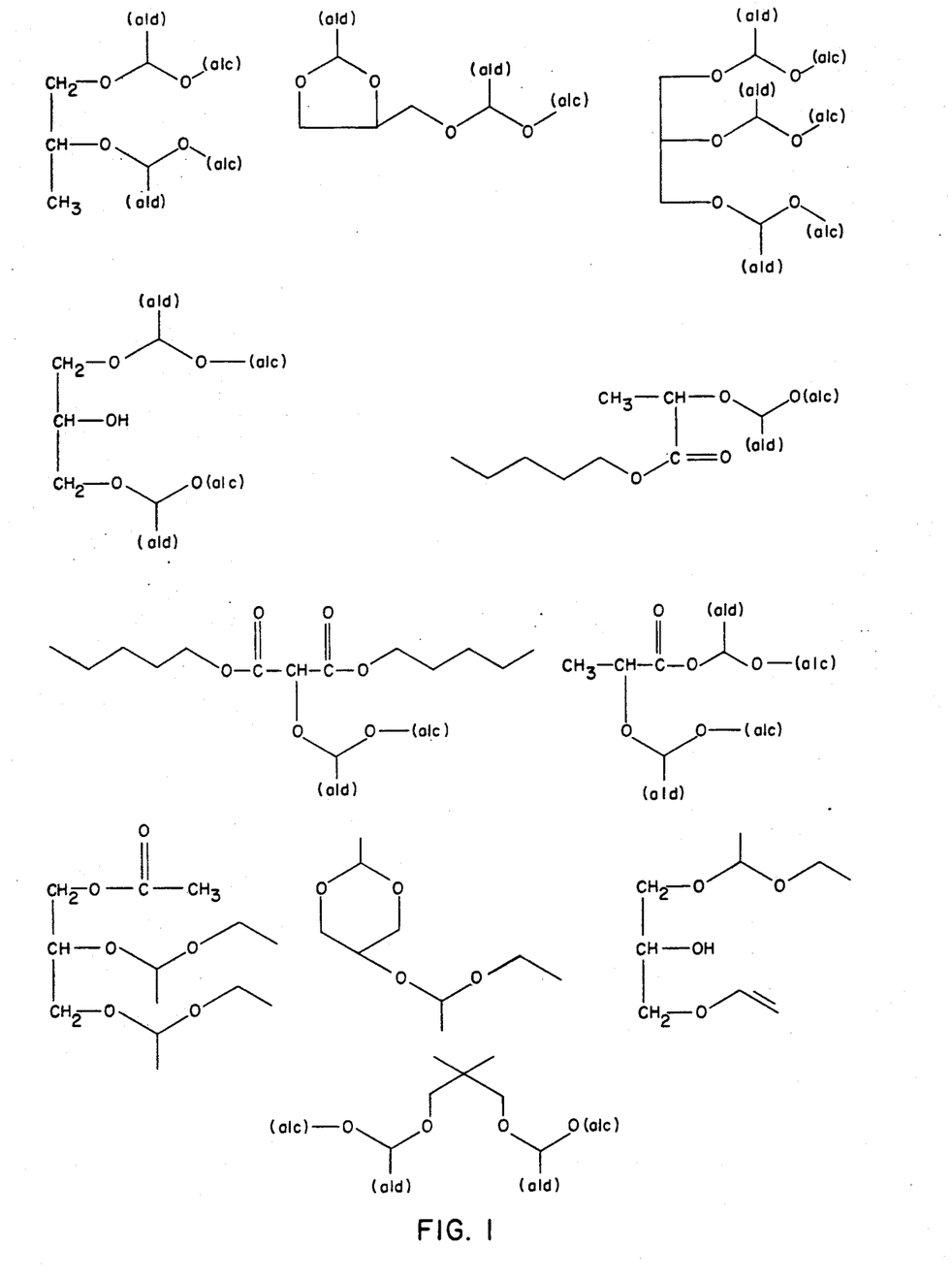
FIG. 1 shows examples of acetals of structures A and B of this invention.
Figure 2:
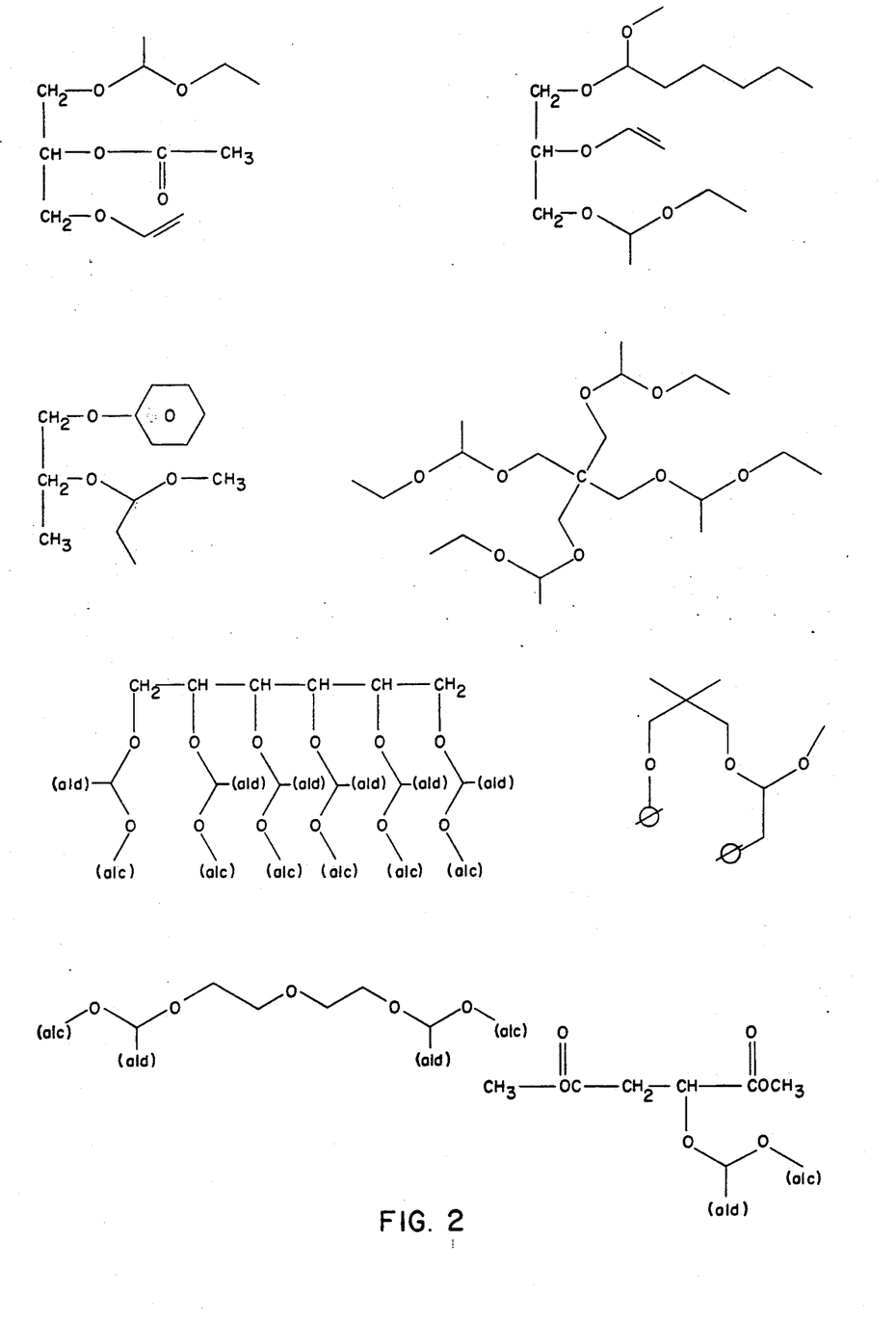
FIG. 2 shows examples of acetals of structures A and B of this invention.

Acetals conforming to the above structures A and B are exemplified by but not limited to the types depicted in FIGS. 1 and 2 where (ald) represents a 1 to 12 carbon alkyl moiety and (alc) represents a 1 to 5 carbon alkyl moiety, a cyclohexyl moiety, or a benzyl moiety.

The acetals of type A can be synthetized by reaction of the appropriate vinyl alkyl ether with the desired polyol in the presence of an acid catalyst as exemplified by the reaction of propylene glycol (I) with propenyl ethyl ether (II) to form Compound III structure (1,2-di (1'-ethoxy)propoxy propane)

The polyols or high molecular weight mono alcohols found useful include propylene glycol, 1,3-propane diol, glycerine, mannitol, sorbitol, neopentyl glycol, pentaerythritol, diethylene glycol monomethyl ether, hexamethylene glycol, diethyl malate, or any other relatively bland mono alcohol or polyol capable of forming a linear acetal through reaction with a vinyl ether.

Figure 3:
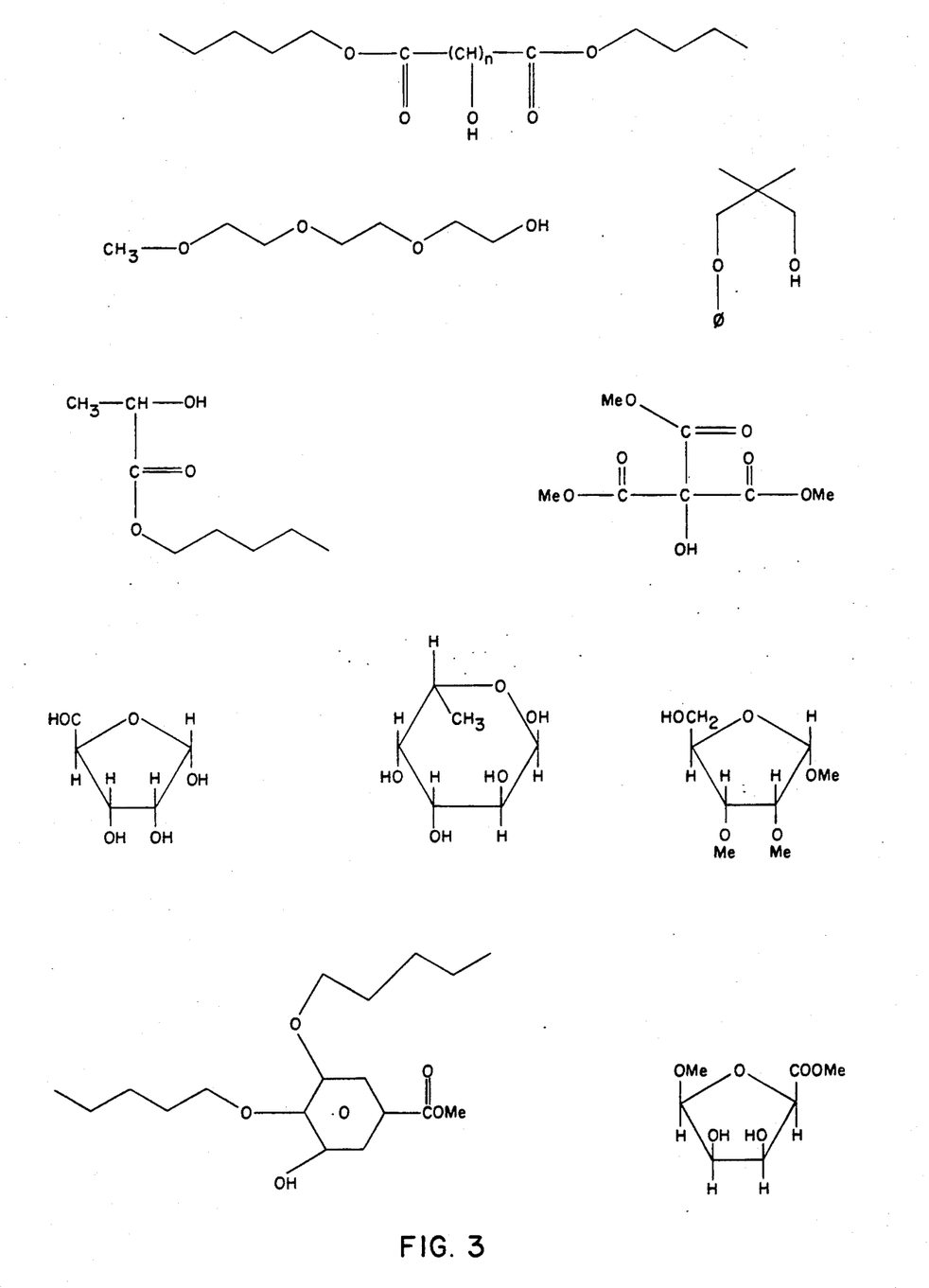
FIG. 3 shows additional examples of structures of mono- or polyols of this invention.

The structures depicted in FIG. 3 are additional, but by no means limiting, types of mono- or polyols, which can be employed. The molecular weight of the mono alcohol or polyol has a practical limit in the weight of the parent acetal derivative relative to the amount of aldehyde which can be released. (ald) and (alc) are as previously described for structures in FIGS. 1 and 2. Typical vinyl ethers which can be employed include ethyl vinyl ether, ethyl propenyl ether, benzyl vinyl ether, cyclohexyl vinyl ether, ethyl butenyl ether, butyl vinyl ether, ethyl hexenyl ether, methyl octenyl ether, and methyl decenyl ether, for example.

Upon searching the literature for methods of synthesizing 1,2,3-tris (1'-ethoxy)ethoxy propane, it was found that the compound had not been made even though there had been several attempts to do so. Several papers have been published on the reaction of ethyl vinyl ether with glycerol and the reaction of glycerol trivinyl ether with alcohols:

(a) M. F. Shostakovsky et al, Bull. Acad. Sci., U.S.S.R., Div. Chem. Sci., 137–40 (1954)
(b) M. F. Shostakovsky et al, ibid., 583–7 (1954)
(c) M. F. Shostakovsky et al, ibid., 313–6 (1955)
(d) M. F. Shostakovsky et al, ibid., 317–20 (1955)

Thus, 1,2,3-tris-(1'-ethoxy)ethoxy propane IV does appear in the literature as a target compound, but attempts at its synthesis have failed. It was postulated to be unstable, decomposing to give the dioxolane V (4-(1'-ethoxy)ethoxymethyl-2-methyl-1,3-dioxolane), when reacting ethyl vinyl ether with glycerol under the influence of an acid catalyst or when reacting glycerol trivinyl ether with ethanol:

In both the syntheses employing glycerol trivinyl ether and ethyl vinyl ether, the reaction mixtures were allowed to reach their natural temperature upon combining all reagents. The exothermic reaction raised the temperature in each case to between 75° and 95° C. It has been found that, surprisingly, when the reaction temperature is kept below about 120° C. and the vinyl ether reagent is always maintained at about an equivalent molar ratio in relation to the moles of alcohol reactant, by concurrent addition of alcohol and vinyl ether, the formation of cyclic products is suppressed. Thus, by concurrent dropwise addition of four moles of ethyl vinyl ether and one mole of glycerine into a reaction flask containing hydrochloric acid catalyst and a solubilizing mixture made up of the dimethyl ether of diethylene glycol and trimethyl hexadecyl ammonium chloride, one is able to form Compound IV, which has not previously been synthesized.

It has also been found that the analogous reaction can be successfully performed on other polyhydroxy compounds, such as propylene glycol, mannitol, sorbitol and the like to give the corresponding multilinear acetals. Since materials such as mannitol and sorbitol are not soluble in ethyl vinyl ether, the reaction can be facilitated by use of a non-reactive cosolvent for the polyhydroxy compound, such as dimethylformamide, hexamethylphosphoric triamide, dimethyl sulfoxide, or N-methyl-2-pyrrolidone. The multilinear acetals derived from polyols are a new class of compounds heretofore inaccessible by known synthetic techniques. The above-described synthetic method has been used with glycerine and ethyl vinyl ether to give the tris-linear acetal IV in 31% yield admixed with acetal V which was obtained in 36.4% yield, or with propylene glycol to give the dilinear acetal VI in 67% yield, and with mannitol in N-methyl-2-pyrrolidone solvent to give acetal VII (1,2,3,4,5,6-hexa (1'-ethoxy)ethoxy hexane) in approximately 70% yield.

To prepare acetals of structure type B, a monohydroxy compound is reacted with an appropriate alkyl vinyl ether as shown below where $R_2$ and $R_3$ are as previously described and $R_7$ is $R_1$ less one carbon atom:

Alternatively, the acetal of type B can be synthesized by reaction of the appropriate alcohol or mixture of alcohols directly with the aldehyde sought to be fixed:

In accordance with the invention a compound is provided, of the general formula:

$$R-(-O-\underset{\underset{R_1}{|}}{CH}-OR_2)_n$$

wherein R is a 3 to 6 (i.e. 3, 4, 5 or 6) carbon linear multivalent hydrocarbon radical having an  moiety attached to at least two of the carbons;

n is an integer greater than one;

$R_1$ is a hydrocarbon radical having from 1 to 14 (i.e., 1, 2, 3, 4, 5, 6, 7, 8, 9, 10, 11, 12, 13 or 14) carbons selected from the group consisting of straight or branched chain alkyl and phenyl radicals; and $R_2$ is an aliphatic or cycloaliphatic radical of 1 to 6 (i.e., 1, 2, 3, 4, 5 or 6) carbon atoms, a benzyl radical or an aliphatic acyl group. Each such compound may be used to flavor a foodstuff by admixture thereof in accordance with the method of the invention.

EXAMPLE 1

4-(1'-Ethoxy)Ethoxy Methyl-2-Methyl-1,3-Dioxolane and 1,2,3-tris[(1'-Ethoxy)Ethoxy]Propane Into a 2000 ml. flask, equipped with mechanical stirrer, heating mantle, thermometer, condenser and twin addition funnels, was added 5 ml. of 36% hydrochloric acid and 1.6 ml. of 50% trimethyl trihexadecyl ammonium chloride in isopropyl alcohol. Next, 294.4 g. of glycerine (3.16 m.) and 921.6 g. of ethyl vinyl ether (12.8 m.) were added concurrently dropwise at a proportional rate over a one-hour period between 23° and 39° C. The reaction mixture was homogeneous at this point and had turned yellow. The mixture was then held at reflux with stirring for an additional hour at 40° C. with mild heating. After standing at room temperature for 14 hours, the reaction mixture was then quenched with 10 g. of sodium carbonate with stirring. After distilling off lights to a pot temperature of 110° C. and a head temperature of 56° C. at 760 mm. Hg, the products were flash-distilled under the following parameters to give 588 g. of yellow oil containing 51.4% 1,2,3-tris[(1'-ethoxy)ethoxy]propane (31% yield) and 37.3% 4-(1'-ethoxy)-ethoxy methyl-2-methyl-1,3-dioxolane (36.4% yield):

| Pot Temp. | Head Temp. | Vacuum |
|---|---|---|
| 60–212° C. | 40–144° C. | 10–0.1 mm. Hg. |

The flash distillate was rectified as follows on a 1"×1' Goodloe column, rated at about seven plates:

| Time (hr.) | Pot (°C.) | Head (°C.) | Vacuum (mm. Hg) | Fraction | Weight (g.) | Linear Acetal (%) | Dioxolane (%) | Comments |
|---|---|---|---|---|---|---|---|---|
| 0 | 24 | 23 | 1.8 | | | | | R.R. 2:1 |
| 2.75 | 124 | 48 | 0.10 | 1 | 52.2 | | 96.3 | |
| 3.25 | 129 | 48 | 0.08 | 2 | 50.6 | | 99.7 | |
| 3.83 | 155 | 51 | 0.09 | 3 | 50.4 | | 99.9 | |
| 4.61 | 163 | 49.5 | 0.08 | 4 | 40.7 | | 96.6 | R.R. 20:3 |
| 5.36 | 167 | 58 | 0.08 | 5 | 30.5 | | 97.5 | |
| 5.72 | 170 | 78 | 0.08 | 6 | 13.7 | | 46.7 | |
| 6.14 | 171 | 92 | 0.13 | 7 | 13.3 | 14.6 | | |
| 6.61 | 178 | 98 | 0.10 | 8 | 17.8 | 64.6 | | |
| 7.76 | 184 | 117 | 1.0 | 9 | 57.9 | 98.1 | | |
| 8.08 | 207 | 102 | 0.11 | 10 | 38.3 | 99.5 | | R.R. 10:20 |
| 8.24 | 210 | 105 | 0.13 | 11 | 48.2 | 99.8 | | |
| 8.5 | 210 | 108 | 0.11 | 12 | 56.2 | 99.9 | | |
| 8.67 | 211 | 102 | 0.11 | 13 | 58.1 | 99.9 | | |

The purity of the acetals was determined by gas chromatography. For the 1,2,3-tris[(1'-ethoxy)ethoxy]propane, a 6'×¼" stainless steel column was used with 20% SE30 on acid-washed Chromasorb W packing, programmed from 135° C. to 220° C. at 4°/minute, He flow 60 ml./minute, and for the 4-(1'-ethoxy)ethoxymethyl-2-methyl-1,3-dioxolane, a 20% Carbowax 20 m. column was used with the remaining parameters the same.

Spectral and Physical Data (A) 1,2,3-tris[(1'-ethoxy)ethoxy]propane $$d\frac{25}{25} \; 0.9561 \quad n_D^{20} \; 1.4222$$

B.P. 117° C. at 1.0 mm. Hg; 102° C. at 0.11 mm. Hg

NMR Spectrum

Methyl protons (18H)—uneven quartet having its center of gravity at 1.15; alkoxy protons (11H)—broad multiplet having its center of gravity at about 3.48; acetal methine protons (3H)—broad multiplet having its center of gravity at about 4.67.

IR Spectrum (CCl₄ solution)

Strong ether C—O—C stretch bands at 1054 cm$^{-1}$, 1080 cm$^{-1}$, 1095 cm$^{-1}$, and 1133 cm$^{-1}$ (maximum intensity band in the spectrum).

(B) 4-(1'-ethoxy)ethoxymethyl-2-methyl-1,3-dioxolane $$d\frac{25}{25} \; 1.0073 \quad n_{20}^D \; 1.4243$$

B.P. at 0.09 mm. Hg, 51° C.

NMR Spectrum

Multiplet of sharp peaks (6) having its center of gravity at 1.2, 3 methyl groups, 9 protons; broad multiplet extending from 3.1 to 4.3, alkoxy protons, 7 protons; quartet centered at 4.66, linear acetal methine, 1 proton; quarter centered at 5.01, dioxolane acetal methine, 1 proton.

IR Spectrum (CCl₄ solution)

Strong ether C—O—C stretch bands between 980 cm$^{-1}$ and 1200 cm$^{-1}$.

EXAMPLE 2

1,2-di[(1'-Ethoxy)Ethoxy]Propane

Into a 250 ml. flask, equipped with condenser, static nitrogen head, mechanical stirrer, and two addition funnels was charged 8 drops of 36.5% hydrochloric acid, 7 ml. of bis-(2-methoxyethyl) ether and 1 drop of 50% trimethyl hexadecyl ammonium chloride in isopropanol. There was then added dropwise from separate addition funnels concurrently at a proportional rate 43.3 g. of ethyl vinyl ether and 15.2 g. of propylene glycol at 40° C. over 23 minutes. Reflux was continued for two more hours at 40° C., the mixture cooled, and 0.4 g. of solid sodium hydroxide added. The product was distilled directly after first removing lights under vacuum. Distillation was performed on a 14"×10 mm. concentric tube column under the following parameters:

| Time (hr) | Pot Temp. (°C.) | Head Temp. (°C.) | Vacuum (mm. Hg) | Fraction | Weight (%) | Product (%) | Comments |
|---|---|---|---|---|---|---|---|
| 0 | 22 | 20 | 5 | | | | Removal of lights |
| 1.55 | 82 | 28 | 0.03 | | | | ~3 ml. collected |
| 1.62 | 85 | 28 | 0.12 | 1 | 3.1 | 0.2 | |
| 1.98 | 92 | 46 | 0.09 | 2 | 0.54 | 26 | |
| 2.20 | 94 | 49 | 0.08 | 3 | 6.1 | 97 | Discontinued |
| 2.53 | 67 | 20 | 0.04 | | | | Restart |
| 3.21 | 94 | 44 | 0.02 | 4 | 7.3 | 99.7 | |
| 3.34 | 95 | 43 | 0.06 | 5 | 5.5 | 99.9 | |
| 4.79 | 98 | 46 | 0.04 | 6 | 4.3 | 99 | |
| 4.92 | 112 | 47 | 0.04 | 7 | 4.4 | 98 | |
| 5.05 | 126 | 43 | 0.08 | 8 | 1.3 | 99 | |
| 5.34 | 142 | 45 | 0.07 | 9 | 0.14 | 98 | |
| 5.61 | 165 | 50 | 0.1 | 10 | 0.42 | 93 | |
| 5.76 | 165 | 55 | 0.09 | 11 | 0.34 | 75 | |

Yield: 29.5 g. 67.1ƒ molar yield.

Spectral and Physical Data $$d\frac{25}{25} \; 0.9153 \quad n_D^{20} \; 1.4112$$

B.P. 47° at 0.04 mm. Hg

NMR Spectrum

Multiplet with center of gravity at 1.18, 15 protons, methyl groups; broad multiplet with center of gravity at 3.57, 7 protons, hydrogens adjacent to one oxygen; broad multiplet centered at about 4.71, 2 protons, acetal methine protons.

IR Spectrum

Strong ether C—O—C stretch absorptions between 1020 cm$^{-1}$ and 1200 cm$^{-1}$ with maxima at 1061 cm$^{-1}$, 1087 cm$^{-1}$, 1104 cm$^{-1}$ and 1140 cm$^{-1}$.

EXAMPLE 3

1,2-di[(1'-Ethoxy)Propoxy]Propane

A 50 ml. flask equipped with magnetic stirrer, thermometer, addition funnels, condensor, and static nitrogen head was charged with three drops of concentrated hydrochloric acid, 2 g. of diglyme and one drop of 30% aqueous trimethyl hexadecyl ammonium chloride. There was then added concurrently, dropwise, 15 g. of ethyl propenyl ether and 5.1 g. of propylene glycol over a four-minute period. An exotherm to 43° C. was noted at the end of the addition period at which time stirring was allowed to continue with warming to 40° C. for three additional hours. The next day the mixture was warmed and stirred for three more hours, quenched with 4.5 g. of KOH and distilled directly:

| Time (hr.) | Pot (°C.) | Head (°C.) | Vacuum | Fraction | Comments |
|---|---|---|---|---|---|
| 0 | 23 | 23 | | | Lights Removal |
| 0.5 | 49 | 25 | 0.4 | | Lights Removal |
| 1.1 | 74 | 58 | 0.07 | | Lights Removal |
| 2.3 | 83 | 62 | 0.08 | 1 | 0.42 g. 52% product |
| 2.4 | 84 | 63 | 0.08 | 2 | 1.5 g. 95.1% product |
| 2.5 | 89 | 65 | 0.09 | 3 | 2.4 g. 98.9% product |
| 2.7 | 114 | 64 | 0.05 | 4 | 1.4 g. 98.6% product |

The product structure was verified by spectroscopic methods. The IR had a broad band envelope extending between 8.3 and 11 microns, showing maxima at 8.85, 9.4, and 9.65 microns. The NMR showed a complex multiplet extending between 4.2 and 4.6 (2 protons; acetal methines), a complex multiplet extending between 3.1 and 4.0 (7 protons; hydrogens alpha to ether oxygen) and a complex maxima extending between 0.7 and 1.8 having major peaks at 0.87, 1.03, 1.13, and 1.27 (alkyl hydrogens; 19 protons). The mass spectrum is tabulated below:

| Measured Mass | % Int. Base | Measured Mass | % Int. Base | Measured Mass | % Int. Base |
|---|---|---|---|---|---|
| 175 | 0.4 | 97 | 0.0 | 57 | 42.2 |
| 173 | 0.0 | 96 | 0.0 | 56 | 2.0 |
| 161 | 0.0 | 96 | 0.0 | 55 | 2.6 |
| 158 | 0.0 | 94 | 0.0 | 47 | 3.7 |
| 133 | 0.1 | 88 | 4.9 | 46 | 2.5 |
| 131 | 0.2 | 87 | 100.0 | 45 | 12.9 |
| 117 | 0.7 | 86 | 18.3 | 44 | 3.9 |
| 116 | 0.1 | 85 | 0.2 | 43 | 12.7 |
| 115 | 0.6 | 75 | 1.7 | 42 | 7.9 |
| 114 | 0.0 | 72 | 2.0 | 41 | 21.7 |
| 103 | 1.6 | 71 | 0.6 | 40 | 5.6 |
| 101 | 0.3 | 69 | 0.3 | 39 | 11.0 |
| 100 | 0.0 | 61 | 0.2 | 38 | 2.4 |
| 100 | 0.5 | 60 | 2.1 | 37 | 0.7 |
| 99 | 1.3 | 59 | 65.7 | 36 | 2.8 |
| 98 | 0.0 | 58 | 29.4 | 35 | 0.3 |
| 98 | 0.0 | | | | |

EXAMPLE 4

1,2,3,4,5,6-hexa[(1'-Ethoxy)Ethoxy]Hexane

Into a 250 ml. flask, equiped with static nitrogen head and magnetic stirrer, was charged 18.6 g. of mannitol, 100 ml. of N-methyl pyrrolidinone and 64.8 g. of ethyl vinyl ether. There was then added 10 drops of concentrated HCl and the mixture stirred at between 22° and 28° for 4.5 hours and allowed to stand overnight. The next day an infrared spectrum of an appropriately worked up sample showed the virtual absence of hydroxyl absorption and strong ether C—O—C bands. The reaction mixture was poured, with stirring, into 750 ml. of water containing excess NaOH and extracted twice with 150 ml. portions of hexane. Each extract was washed consecutively with two 750 ml. portions of water. The compbined oganic phases were dried over solid sodium carbonate-sodium sulfate and vacuum evaporated at about 10 mm. Hg to give 59 g. of crude oil. Distillation was performed on a short path micro still under the following conditions:

Charge: 19 g. of crude + 0.2 g. of $Na_2CO_3$.

| Time (hr.) | Pot Temp. (°C.) | Head Temp. (°C.) | Vacuum (mm. Hg.) | Fraction | Weight (g.) |
|---|---|---|---|---|---|
| 0 | 55 | 22 | 0.5 | | |
| 0.35 | 185 | 170 | 0.5 | 1 | — |
| 1.35 | 182 | 175 | 0.6 | 2 | 0.2 |
| 1.62 | 184 | 176 | 0.6 | 3 | 0.4 |
| 1.65 | 185 | 176 | 0.6 | 4 | 2.3 |
| 1.70 | 186 | 176 | 0.6 | 5 | 0.7 |
| 1.77 | 187 | 178 | 0.6 | 6 | 4.4 |
| 1.80 | 180 | 174 | 0.6 | 7 | 1.5 |
| 1.83 | 182 | 174 | 0.5 | 8 | 0.8 |
| 1.89 | 186 | 176 | 0.5 | 9 | 3.1 |
| 1.75 | 184 | 175 | 0.5 | 10 | 1.9 |
| 1.78 | 182 | 178 | 0.5 | 11 | 0.6 |

IR Spectrum ($CCl_4$ solution)

Weak, broad band at 3500 $cm^{-1}$ indicating some free hydroxyl; strong C—O—C ether stretch bands extending between 990 $cm^{-1}$ and 1200 $cm^{-1}$ with maxima at 1044 $cm^{-1}$, 1082 $cm^{-1}$ and 1136 $cm^{-1}$.

NMR Spectrum ($CCl_4$ solution, TMS reference)

Non-symmetrical quartet extending from 1.0 to 1.4 with center of gravity about 1.25, methyl protons—34.5 protons (theory 36); broad multiplet extending between 3.2 and 4.0 having a center of gravity about 3.6, hydrogens on monoalkoxy substituted carbons, 20 protons; broad complex multiplet extending between 4.45 and 5.1, having its center of gravity at about 4.75, acetal methine protons, 5.5 protons (theory 6.0). A spectrum run in $CDCl_3$ showed the methyl to alkoxy to acetal methine proton ratios to be 33.9/20/5.9. A $d_4$-MeOD exchanged spectrum changed the ratio to 32.8/20/5.7 while a $d_6$-DOAc exchanged spectrum showed the ratios to be 34.9/20/5.9. Oximation analysis of acetal hydrolyzed at pH 3.5 in the presence of hydroxylamine showed 96.4% of the theoretical acetaldehyde to be generated, indicating no more than 20% of the sixth hydroxyl in the molecule to be free OH.

EXAMPLE 5

Diethyl 2-[(1'-Ethoxy)Ethoxy]Succinate

A mixture of 19 g. diethyl malate and 0.1 g. of 36% hydrochloric acid was added to a 50 ml. round-bottom flask equipped with an addition funnel, static nitrogen head, condenser, heating mantle, thermometer, and magnetic stirrer. Ethyl vinyl ether was then added, dropwise, at 41° to 43° C. over a one-hour period and quenched with 0.4 g. of solid sodium carbonate. Distillation was performed directly on the mixture (short path column):

| Time (hr.) | Pot (°C.) | Head (°C.) | Vacuum | Fraction | Weight (g.) | Comments |
|---|---|---|---|---|---|---|
| 0 | 43 | 24 | 0.4 | | | Lights Removal |
| 2 | 99 | 79 | 0.1 | | | Distilling over |
| 2.1 | 100 | 80 | 0.1 | 1 | 1.8 | |

-continued

| Time (hr.) | Pot (°C.) | Head (°C.) | Vacuum | Fraction | Weight (g.) | Comments |
|---|---|---|---|---|---|---|
| 2.4 | 101 | 83 | 0.1 | 2 | 3.8 | |
| 2.9 | 102 | 85 | 0.2 | 3 | 5.9 | |
| 3.1 | 106 | 90 | 0.1 | 4 | 5.2 | |
| 3.4 | 117 | 87 | 0.4 | 5 | 3.4 | |

The above fractions were combined for redistillation through a one-foot concentric tube column:

| Time (hr.) | Pot (°C.) | Head (°C.) | Vacuum (mmHg) | Fraction | Weight (g.) | Comments (0.5 g. solid) NA CO in pot) |
|---|---|---|---|---|---|---|
| 0 | 120 | 21 | 0.06 | | | 30:1 RR |
| 1.5 | 135 | 77 | 0.08 | 1 | 2.3 | 10:2 RR |
| 1.9 | 137 | 76 | 0.08 | 2 | 5.2 | 20:2 RR |
| 3.2 | 140 | 76 | 0.07 | 3 | 3.4 | |
| 3.5 | 140 | 77 | 0.07 | 4 | 1.7 | |
| 4.4 | 155 | 87 | 0.08 | 5 | 3.1 | |
| 4.9 | 240 | 65 | 0.08 | 6 | 1.6 | |

The structure was verified by spectroscopic methods. The NMR spectrum showed a multiplet extending from 0.9 to 1.4 with the major peak at 1.51 (terminal methyls, 12 protons), a doublet at 2.65 and 2.74 (methylene alpha to a carbonyl, 2 protons); a multiplet (ten peaks - a doubled pentuplet), extending from 3.25 to 3.8 centered at 3.5 (2 protons, methylene adjacent to acetal group), octet extending between 3.9 and 4.35 (4 protons, ester methylenes attached to oxygen), multiplet extending between 4.35 and about 4.6 (1 proton, alpha carbonyl methine) and a multiplet extending between 4.6 and 4.95 (1 proton, acetal methine).

EXAMPLE 6

1'-Ethoxyethyl-2-(1''-Ethoxyethoxy)Propionate

A solution of 18 g. of lactic acid in 100 g. of N-methyl pyrrolidone and 8 drops of 36% hydrochloric acid was added to a round-bottom flask equipped with mantle, magnetic stirring, condensor, thermometer, static nitrogen head and addition funnel. Ethyl vinyl ether was added, dropwise, over a 26-minute period at between 46° and 65° C. pot temperature. After one-half hour of additional heating at 50° C., the mixture was allowed to stand over the weekend. The mixture was then combined with 100 ml. of hexane in a separatory funnel and washed with dilute sodium carbonate solution. The organic phase was dried over sodium sulfate and the light fractions were evaporated under vacuum. The material was then distilled through a micro-vigreaux column:

| Time (hr.) | Pot (°C.) | Head (°C.) | Vacuum (mmHg) | Fraction | Weight (g.) | Comments |
|---|---|---|---|---|---|---|
| 2.5 | 90 | 31 | 0.07 | | | Light fractions removal |
| 3.0 | 103 | 47 | 0.08 | | | RR 20:2 |
| 3.1 | 105 | 59 | 0.07 | 1 | 3.7 | 67% product |
| 3.3 | 107 | 60 | 0.07 | 2 | 2.3 | 87% product |
| 3.5 | 113 | 62 | 0.07 | 3 | 1.8 | 90% product |
| 3.7 | 123 | 65 | 0.07 | 4 | 1.1 | 98% product |
| 4.7 | 145 | 45 | 0.04 | 5 | 1.2 | 72% product |

The structure was confirmed by spectroscopic techniques. The NMR showed a multiplet extending from 1.0 to 1.6 (15 protons, terminal methyls), a complex multiplet extending between 3.3 and 3.9 (4 protons, methylenes attached to ether oxygen), a quartet centered at 4.33 (alpha carbonyl methine attached to ether oxygen, 1 proton), a quartet centered at 4.79 (1 proton, acetal methine) and a quartet centered at 5.98 (1 proton, acetal methine, in which the acetal is attached to the carbonyl).

EXAMPLE 7

1,2-di[(1'-Butoxy)Ethoxy]Propane

A round-bottom flask equipped with static nitrogen head, magnetic stirrer, thermometer, and addition funnels was charged with 5 g. of tetrahydrofuran and 4 drops of 36% HCl. Propylene glycol (30 g.) and 120 g. of n-butyl vinyl ether were added, dropwise, concurrently in stoichiometric proportion with cooling at 20° to 26° C. over 1.1 hours. Solid sodium carbonate was added to quench the reaction and distillation was performed directly on a concentric tube column:

| Time (hr.) | Pot (°C.) | Head (°C.) | Vacuum (mmHg) | Fraction | Weight (g.) | Comments |
|---|---|---|---|---|---|---|
| 0 | — | — | 250 mm | | | Light fractions removal |
| 1.8 | 101 | 54 | " | | | 30:RR |
| 2.9 | 106 | 61 | " | 1 | 4.8 | |
| 3.9 | 111 | 65 | " | 2 | 11.6 | |
| 4.5 | 115 | 65 | " | 3 | 7.7 | |
| 5.8 | 135 | 61 | " | 4 | 11.9 | |
| 6.3 | 138 | 61 | " | 5 | 36.9 | |
| 8.2 | 140 | 46 | 133 | 6 | 9.0 | |
| 9.7 | 124 | 57 | 10 | 7 | 2.4 | |
| 11.2 | 135 | 61 | 10 | 8 | 11.9 | |
| 11.8 | 134 | 66 | 0.5 | 9 | 7.6 | |
| 14.1 | 143 | 86 | 0.5 | 10 | 7.4 | |
| 15.2 | 143 | 87 | 0.5 | 11 | 14.1 | |
| 16.3 | 139 | 86 | 0.5 | 12 | 4.8 | |
| 17.3 | 148 | 87 | 0.5 | 13 | 13.6 | 30:3 RR |
| 21.3 | 154 | 85 | 0.5 | 14 | 27.8 | Total takeoff |
| 23.4 | 165 | 85 | 0.5 | 15 | 6.5 | |

Fractions 11 through 15 were bulked, the bulking found by GLC to be 98.6% pure on 20% SE 30 on Chromasorb W packing in a six-foot by one-quarter inch column programmed from 100° to 220° C. at 8°/minute. The product structure was verified by spectroscopic techniques. The NMR spectrum showed a broad distorted triplet centered at 0.93 (6 protons, terminyl chain methyls), a doublet centered at 1.29, splitting 2.8 c.p.s. (methyls attached to acetal methine), the entire methyl and methylene envelope extending from 0.78 to 1.8 (23 protons), a broad multiplet extending between 3.2 and 3.75 centered at about 3.47 (6 protons, methylenes attached to oxygen); a broad quartet centered at 3.88, extending between 3.75 and 4.0 with the major apparent splitting equal to 6 c.p.s. (1 proton, ether methine), broad multiplet extending between 4.6 and 4.95 (2 protons, acetal methine). The mass spectrum is tabulated below:

| Measured Mass | % Int. Base | Measured Mass | % Int. Base |
|---|---|---|---|
| 131.11 | 1.3 | 57.07 | 79.5 |
| 130.10 | 1.2 | 56.07 | 53.2 |
| 103.08 | 5.7 | 55.06 | 10.0 |
| 102.10 | 4.8 | 53.04 | 1.2 |
| 101.10 | 65.8 | 46.04 | 2.3 |
| 100.09 | 5.8 | 45.03 | 100.0 |
| 87.04 | 16.4 | 44.03 | 22.1 |
| 85.06 | 11.3 | 43.04 | 45.8 |
| 83.08 | 3.7 | 42.05 | 14.9 |
| 73.06 | 1.1 | 41.04 | 83.3 |
| 72.06 | 2.4 | 40.04 | 2.6 |
| 71.05 | 2.1 | 39.03 | 11.4 |
| 65.05 | 2.3 | 33.04 | 1.7 |
| 61.03 | 2.5 | 32.00 | 4.5 |
| 59.05 | 26.9 | 31.02 | 35.7 |
| 58.05 | 14.3 | | |

EXAMPLE 8

Ethyl 2-[(1'-Methoxy)]n-Decyloxy Propionate

Into a 50 ml. round-bottom flask equipped with a static nitrogen head, thermometer, mantle, and magnetic stirrer, was charged 10.2 g. of methyl decenyl ether and 3.5 g. of ethyl lactate. One drop of HCl was added after heating the mixture to 40° C., whereupon an exotherm to 63° C. was experienced. Stirring was continued for 2.3 hours at between 40° and 53° C. The mixture was quenched with solid sodium carbonate. Another run made with 20.4 g. of the methyl decenyl ether and 7.1 g. of ethyl lactate was performed in a similar manner and combined with the above run for workup. The product was distilled on a one-foot microvigreaux column:

| Time (hr.) | Pot (°C.) | Head (°C.) | Vacuum (mmHg) | Fraction | Weight (g.) | Comments |
|---|---|---|---|---|---|---|
| 0.3 | 71 | 25 | 0.6 | | | Light fractions removal |
| 2.6 | 119 | 85 | 5 | 1 | 3.3 | |
| 2.9 | 124 | 86 | 5 | 2 | 3.6 | |
| 3.5 | 135 | 90 | 6 | 3 | 3.9 | |
| 3.8 | 145 | 96 | 4 | 4 | 2.3 | |
| 4.3 | 158 | 104 | 4.5 | 5 | 2.5 | |
| 7.3 | 147 | 77.5 | 1 | 6 | 14.1 | 75% purity |
| 7.8 | 180 | 130 | 1 | 7 | 2.7 | |

EXAMPLE 9

1-Benzyloxy-1-isobutoxy Ethane

A 250 ml. round-bottom flask equipped with a magnetic stirrer, condensor, mantle, and addition funnel was charged with 52.5 g. of benzyl alcohol and 4 drops of 36% hydrochloric acid. The mixture was heated to 40° C. and 50 g. of isobutyl vinyl ether was added dropwise, over a one-half hour period. GLC analysis showed the reaction to be complete at this point. Saturated sodium carbonate solution was added to quench (10 ml.) and the organic phase was dried over sodium sulfate prior to distillation on a concentric tube column:

| Time (hr.) | Pot (°C.) | Head (°C.) | Vacuum (mmHg) | Fraction | Weight (g.) | Comments |
|---|---|---|---|---|---|---|
| 0 | | | 10 mm | | | Lights removal |
| 3.5 | 127 | 45 | 5 | | | RR 30:3 |
| 3.8 | 131 | 87 | 5 | 1 | 6.4 | RR 30:6 |
| 5.2 | 132 | 88 | 5 | 2 | 7.2 | |
| 7.7 | 132 | 90 | 5 | 3 | 6.1 | 99.1% product |
| 9.6 | 132 | 90 | 5 | 4 | 18.1 | |
| 10.4 | 135 | 90 | 5 | 5 | 28.6 | |
| 11.4 | 160 | 88 | 5 | 6 | 21.9 | Purity 99+% |

The acetals of this invention generate their corresponding aldehyde, in the manner of linear acetals generally, by response to an acidic pH condition in the foodstuff to which they are added. The rate at which the acetal undergoes hydrolysis to release the aldehyde is a function of the pH and the temperature. For example, at pH 4.0 and 25° C., the acetal, 1,2-di[(1'ethoxy)ethoxy]propane, is 32.5% hydrolyzed within 30 minutes. At pH 4.6 and 100° C., it is 67% hydrolyzed after two hours. It can thus be seen that a relatively wide selection of hydrolysis conditions and rates can be selected to fit the conditions of preparation of specific foodstuffs.

EXAMPLE 10

Hydrolysis Study on Various Acetals

Test (a)-4-(1'-ethoxy)ethoxymethyl-2-methyl-1,3-dioxolane

The title acetal (0.224 g.) was dissolved in 50 ml. of dilute sulfuric acid at pH 3.0. The solution absorbence was measured by ultraviolet spectroscopy at 275 giving the following data points relative to theoretical acetaldehyde generation. This test showed that essentially only the linear acetal portion of the molecule released at this pH and temperature:

| Time (min.) | Absorbence | | % Acetaldehyde Generated | |
|---|---|---|---|---|
| | Run 1 (Theor. 0.197) | Run 2 (Theor. 0.175) | Run 1 | Run 2 |
| 2 | 0.050 | 0.012 | 25.4 | 6.9 |
| 4 | 0.072 | 0.04 | 36.5 | 22.9 |
| 10 | 0.116 | 0.1 | 58.9 | 57.1 |
| 20 | 0.164 | 0.14 | 83.2 | 81.1 |
| 30 | 0.193 | 0.15 | 98.0 | 85.7 |

Test (b)-1,2,3-tris[(1'-ethoxy)ethoxy]propane

In a manner similar to that used in Test (2), except that the acetal was solubilized by using 10% ethanol, the title acetal was subjected to hydrolysis under various pH conditions. The results are tabulated below:

| Time (min.) | Absorbence | | | % Acetaldehyde Generated | | |
|---|---|---|---|---|---|---|
| | Run 1 (pH 3) (Theor. 0.297) | Run 2 (pH 3.5) (Theor. 1.75) | Run 3 (pH 3) (Theor. 0.35) | Run 1 (pH 3) | Run 2 (pH 3.4) | Run 3 (pH 3.5) |
| 1 | — | — | 0.058 | — | — | 16.6 |
| 2 | 0.033 | — | 0.061 | 11.1 | — | 17.4 |
| 4 | 0.083 | — | 0.090 | 27.9 | — | 25.7 |
| 5 | — | 0.046 | — | — | 26 | — |
| 10 | 0.202 | 0.077 | 0.173 | 68.0 | 44 | 49.4 |
| 20 | 0.285 | 0.121 | 0.260 | 95.6 | 69 | 74.3 |
| 25 | — | — | 0.280 | — | — | 80.0 |
| 30 | 0.307 | 0.15 | — | 103.0 | 86 | — |
| 37 | — | 0.158 | — | — | 90 | — |

Test (c)

In a manner similar to that used in Test (a), 1,2-di[(1'-ethoxy)ethoxy]propane was subjected to hydrolysis at various pH levels in dilute sulfuric acid:

| Time (min.) | Run 1 (pH 3) (Theor. 0.354) | Run 2 (pH 3.1) (Theor. 0.347) | Run 3 (pH 3.2) (Theor. 0.358) | Run 4 (pH 3.4) (Theor. 0.35) | Run 5 (pH 3.5) (Theor. 0.356) | Run 6 (pH 4) (Theor. 0.366) |
|---|---|---|---|---|---|---|
| | Absorbence | | | | | |
| 1 | 0.03 | 0.03 | 0.03 | — | — | — |
| 2 | 0.07 | 0.07 | 0.055 | 0.017 | — | 0.005 |
| 4 | 0.15 | 0.145 | 0.114 | 0.041 | 0.068 | 0.012 |
| 10 | 0.33 | 0.327 | 0.274 | 0.128 | 0.125 | 0.034 |
| 20 | — | — | — | 0.252 | 0.209 | 0.076 |
| 30 | — | — | — | 0.030 | 0.255 | 0.119 |
| 40 | — | — | — | — | — | 0.155 |
| | % Acetaldehyde Generated | | | | | |
| 1 | 8.5 | 8.6 | 8.4 | — | — | — |
| 2 | 19.4 | 20.2 | 15.4 | 4.9 | — | 1.4 |
| 4 | 42.4 | 41.8 | 31.8 | 11.7 | — | 3.3 |
| 10 | 93.2 | 94.2 | 76.5 | 36.6 | — | 9.3 |
| 20 | — | — | 100 | 72.0 | 58.7 | 20.8 |
| 30 | — | — | — | 85.7 | 71.6 | 32.5 |
| 40 | — | — | — | — | — | 42.3 |

EXAMPLE 11

Hydrolysis of 1,2-di[(1'-Ethoxy)Ethoxy]Propane at pH 4.6

A 99.5 g. portion of water in an ether bottle was adjusted to pH 4.6 using hydrochloric acid. The acid solution was brought to between 90° and 95° C. and 0.5 g. of 1,2-di[(1'-ethoxy)ethoxy]propane was added just prior to sealing the bottle, which contained a magnetic stirrer. The solution was heated to 100° C. for 1.5 minutes and quenched in an ice bath. U.V. spectrophotometry showed a value of 0.38 absorbance versus 0.40 theoretical absorbance, indicating almost 100% hydrolysis of the acetal.

EXAMPLE 12

Hydrolysis of 1,2-di[(1'-Ethoxy)Ethoxy]Propane at pH 6.5

A 99.5 g. portion of water in an ether bottle was adjusted to pH 6.5 with hydrochloric acid. The acid solution was heated to between 90° and 95° C. and 0.5 g. of 1,2-di[(1'-ethoxy)ethoxy]propane was added just prior to sealing the bottle, which contained a magnetic stirrer. The solution was heated at 100° C. for two hours and then cooled. U.V. spectrophotometry showed a value of 0.27 absorbance versus 0.40 theoretical for 100% hydrolysis of the acetal. This corresponds to about 67% hydrolysis of the acetal.

EXAMPLE 13

Hydrolysis of 1,2-di[(1'-Ethoxy)Ethoxy]Propane at pH 7.5

A 99.5 g. portion of water in an ether bottle was adjusted to pH 7.5 with potassium hydroxide. The basic solution was heated to between 90°-95° C. and 0.5 g. of 1,2-di[(1'-ethoxy)ethoxy]propane was added just prior to sealing the bottle, which contained a magnetic stirrer. The solution was heated at 100° C. for five hours with stirring, then cooled. U.V. spectrophotometry showed an absorbance value of 0.380 versus 0.400 theoretical, indicating almost 100% hydrolysis of the acetal.

EXAMPLE 14

Hydrolysis of 4-(1'-Ethoxy)Ethoxy Methyl-2-Methyl-1,3-Dioxolane at pH 3.0

A 99.57 g. portion of water in an ether bottle was adjusted to pH 3.0 with hydrochloric acid. The acid solution was heated to between 90°-95° C. and 0.43 g. of 4-(1'-ethoxy)ethoxy methyl-2-methyl-1,3-dioxolane was added just prior to sealing the bottle, which contained a magnetic stirrer. The solution was heated at 100° C. for one hour and then cooled. U.V. spectrophotometry showed an absorbance value of 0.370 versus 0.400 theoretical, indicating hydrolysis of both the linear and cyclic acetal functions to almost the 100% level.

EXAMPLE 15

Hydrolysis of 4-(1'-Ethoxy)Ethoxy Methyl-2-Methyl-1,3-Dioxolane at pH 6.5

A 99.57 g. portion of water in an ether bottle was adjusted to pH 6.5 with hydrochloric acid. The acid solution was heated to between 90°-95° C. and 0.43 g. of 4-(1'-ethoxy)ethoxy methyl-2-methyl-1,3-dioxolane was added just prior to sealing the bottle, which contained a magnetic stirrer. The solution was heated at 100° C. for six hours and then cooled. U.V. spectrophotometry showed an absorbance value of 0.160. Hydrolysis of both the linear and cyclic acetal functions would given an absorbance of 0.4. This corresponds to hydrolysis of about 80% of the linear portion of the acetal.

In the absence of the aforementioned acidic environment, the acetals of the invention are extremely stable. They are thus very useful in the preparation of dried, ready mix, or instant food products which create the required acid environment when water or milk is added. The shelf life of such products treated with aldehydes is presently quite low due to volatility or instability of the aldehyde. When the acetals of this invention are used, the shelf life of the product is not limited by the properties of the additive.

Usage of the acetals is not limited, however, to dry products. They are equally useful in liquid products which are stored under conditions whereby the aldehyde is prevented from escaping after it has been generated. One useful such application is in canned fruits and vegetables, from which a large proportion of the natural aldehyde will have been driven off during processing. The acetal can be added immediately prior to the sealing of the container to regenerate the aldehyde lost during processing.

It has been found that the acetals of this invention are useful in generating aldehyde to improve the fresh effect of flavors related to those listed previously. A partial listing of products into which the acetals can be incorporated includes:

| Baked Goods | Foods |
|---|---|
| Biscuits | Beef stew |
| Bread | Breakfast cereal - cooked |
| Cakes | Breakfast cereal - dry |
| Cookies | Canned fruit juices |
| Crackers | Canned fruits & vegetables |
| Donuts | Canned vegetable juices |
| Flan | Cheese |
| Muffins | Cooking oil |
| Pastries | Fruit sauces |
| Beverages | Gravy |
| Beer | Imitation meat dishes |
| Beverage powder | Instant rice mix |
| Beverage powder - milk based | Margarine |
| Beverage powder - sugar free | Mayonnaise |
| Broth drink | Pancake mix |
| Beverage syrup - carbonated | Pet food |
| Coffee - instant | Potatoes |
| Coffee whitener | Salad dressing |
| Cordials | Snack foods |
| Liquor | Soup |
| Milk | Sour cream |
| Still beverage | Sour cream mix |
| Tea | Soy sauce |
| Wine | Table syrup |
| Confectioneries | Tomato sauce & paste |
| Chewing gum | Yogurt |
| Chocolate | Frozen Foods |
| Fondant | Frozen fruit juices |
| Frosting | Ice cream |
| Hard candy | Ice pops |
| Marshmallow | Pharmaceuticals |
| Jelly & preserves | Antacid |
| Pressed Tablets | Mouth freshener |
| Summer Coating (compound coating) | Mouthwash |
| Desserts | Tablets - aspirin |
| Custard | Syrup - cough |
| Carageenan gel | Syrup - other |
| Dips | Toothpaste |
| Gelatin dessert | Tobacco |
| Pie filling | Chewing |
| Pudding - cooked | Cigar |
| Pudding - instant | Cigarette |
| Topping syrup | Pipe |
| Whipped Toppings | |

The amount of the aldehyde-generating acetal employed should be sufficient to impart the desired flavor impact to the foodstuff to which they are added. A small but effective amount is sufficient. The precise amount will vary, of course, according to the food composition to be flavored and also upon the aldehyde to be generated. In general, the organoleptically useful range of acetal addition is between about 5 and 1000 p.p.m., depending upon the foodstuff, the flavor impact sought, and the acetal to be generated. Parts are expressed as parts by weight based on the weight of the foodstuff.

Most of the acetals are liquids at ordinary temperatures. They can accordingly be used in their natural state when they are intended to be hydrolyzed substantially immediately, e.g., when they are added to an acidic liquid environment.

The acetals can, however, readily be incorporated into non-toxic, flavor-indifferent matrix materials to encapsulate them. Spray drying in a starch matrix is a preferred encapsulation technique. Encapsulating a liquid acetal is particularly desirable when it is to be incorporated into a dry material, e.g., a beverage powder. The solid form of the encapsulated acetal greatly facilitates handling and uniform incorporation of the acetal into the product.

EXAMPLE 16

A citrus drink was prepared at about 23° C. by combining 8 drops of a 1% solution of orange flavor in 95% ethanol and 14 ml. of citric syrup and bringing to volume with water in a 4 oz. container (about 114 g. of water was used). The orange flavor was orange terpenes containing 5% by weight of acetaldehyde. The citric syrup was made by adding to 1 gallon of 67.5% sucrose in water, 14 ml. of a 25% by weight solution of sodium benzoate in water and 44 ml. of 50% citric acid in water. The pH of this syrup is normally about 3.1. A second drink was formulated using, as the orange flavor, orange terpenes containing 12% of 4-(1'-ethoxy)ethoxymethyl-2-methyl-1,3-dioxolane.

Out of a panel of five professional flavorists four determined the flavor differences to be small between the drinks and the fifth judged the generator-fortified drink to be better on a blind selection basis. On a re-test the following day with freshly prepared drinks, tested within 20 minutes to ½ hour of mixing, only one flavorist out of five was able to identify the fortified drink on a blind selection basis.

EXAMPLE 17

Test (a)

Citrus drinks were prepared in the same manner as in Example 16 using in Drink No. 1 a non-fortified orange flavor, in Drink No. 2 the same orange flavor fortified with 7.7% of 4-(1'-ethoxy)ethoxymethyl-2-methyl-1,3-dioxolane, and in Drink No. 3, 7.7% 1,2,3-tris (1'-ethoxy)ethoxy propane. Four professional flavorists were asked to rate the drinks in order of "freshness" effect with the following results:

| | Test Time* | Rating |
|---|---|---|
| Flavorist 1 | 1-2 minutes | Drink 2 Drink 1, Drink 3 |
| Flavorist 2 | 2 minutes | Drink 2 Drink 1, Drink 3 |
| Flavorist 3 | About 2 min. | Drink 3 Drink 1, Drink 2 |
| Flavorist 4 | About 10 min. | Drink 2 Drink 3, Drink 1 |

*Time interval between mixing and tasting

This test showed a predominant preference for the generator-fortified beverages.

Test (b)

Two orange drinks were prepared for the method described for Test (a) whereby an orange flavor fortified with 8% 1,2,3-tris-[(1'-ethoxy)ethoxy]propane was compared to one without acetaldehyde or generator present. As in Example 5 and Example 6(a), the drinks were made up at ambient temperature, approximately 23° C. Within two minutes after the drinks were prepared, all 4 professional flavorists stated their preference to be the generator-fortified beverage because of its "fresh-juice" effect.

Test (c)

Two orange-flavored drinks were prepared as in Test (b). One drink was an orange flavor fortified with 8% 1,2,3-tris[(1'-ethoxy)ethoxy]propane and the other without generator or acetaldehyde. The water used to make up the beverages was pre-chilled to 10° C. and the flavor oil in alcohol at 1% was added to the beverage after the citric syrup was mixed in. Again, all 4 professional flavorists found the generator-fortified beverage within 2 minutes after mixing to be preferred as having a "fresh-squeezed" juice effect. Two of the flavorists found the effect noticeable within 1 minute.

EXAMPLE 18

Cup Cake Flavor Enhancement using 1,2-di[(1'-Ethoxy)Ethoxy]Propane

A batter mix comprised of 5.5 ounces of water, one egg and one and three quarters cups of cake mix (pH 6.5) was mixed with a hand beater until smooth. Orange flavor was then mixed in at 0.125%. The title acetaldehyde generator was spray-dried in a starch matrix such that an 8.7% acetaldehyde equivalent was obtained. The spray-dried product was dispersed in water to make a 10% solution and this solution added to aliquots of the cake mix at 0.05 and 0.1% respectively. The aliquots were baked into cup cakes along with a control for 20 minutes at 350° F. The generator improved the impact of the orange flavor in the cake and made it appear as a fresher orange flavor.

EXAMPLE 19

Orange Breakfast Drink Mix Enhancement using 1,2-di[(1'-Ethoxy)Ethoxy]Propane

A dry beverage powder was made up of the following ingredients:

| Material | Parts by Weight |
|---|---|
| Sucrose | 865.3 |
| Citric Acid | 50.0 |
| Ascorbic Acid | 10.0 |
| Potassium Citrate | 20.0 |
| Carboxymethyl cellulose (D.S. 0.7) | 1.6 |
| Gum Arabic | 13.0 |
| Clouding Agent | 25.0 |
| FD & C Yellow #5 (10% in lactose) | 4.0 |
| FD & C Yellow #6 (1% in lactose) | 8.0 |
| Artificial Orange Flavor | 3.1 |
| | 1000.0 |

One quart of water was mixed with 165 g. of the above beverage mix formulation. The pH was 2.8. This control drink was compared to drinks fortified with $4.4 \times 10^{-3}$ g/liter and $8.8 \times 10^{-3}$ g/liter respectively of the title generator. The generator fortified drinks showed an improved fresh juice flavor effect when compared to the control.

EXAMPLE 20

Enhancement of Red Fruit Punch Dry Mix using 1,2-di[(1'-Ethoxy)Ethoxy]Propane

A mixture of 104 g. Hawaiian Punch Dry Mix (red fruit) was combined with 946 g. of water and then $8.8 \times 10^{-3}$ g. of the title generator compound was added per 1050 g. of beverage. The beverage had a pH of 3.3. The generator fortified beverage had a stronger impact and fresher fruit juice effect when compared to a non-fortified control.

EXAMPLE 21

Gelatin Dessert Flavor Enhancement using 1,2-di[(1'-Ethoxy)Ethoxy]Propane

A control sample gelatin dessert was made in the following manner using commercial orange-flavored Jello (General Foods trademark). An 85 g. package was dissolved in 236 g. of boiling water and 236 g. of cold water was then added. The mixture was chilled until it was set. A second flavor enhanced gelatin dessert was made in the same manner except that 0.01% of the same spray-dried generator described in Example 8 was added to the dessert mix prior to dissolving it in boiling water. The generator enhanced dessert had much more of a "fresh juice" taste when compared to the control. The pH of the gelatin dessert was 3.86.

EXAMPLE 22

Simulated Yogurt Beverage Flavor Enhancement using 1,2-di[(1'-Ethoxy)Ethoxy]Propane A milk-based beverage powder was formulated as follows:

| | |
|---|---|
| Non-fat dry milk solids | 48.00 g. |
| Sucrose | 46.00 |
| Sodium Citrate | 2.50 |
| Strawberry | 1.25 |
| Yogurt Flavor | 1.10 |
| Citric Acid | 0.82 |
| FD & C Red #40 (1% in lactose) | 0.12 |
| Carageenan | 0.10 |

The above mixture (40 g.) was blended in an electric blender with eight ounces of milk for ten seconds. The pH was 6.2.

A second beverage was made up in the same manner except 0.014 g. of the same spray-dried generator described in Example 8 was added prior to blending. Four out of four professional flavorists were able to discern the difference between the enhanced beverage and the control, three of whom stated that a much improved fresh effect was present with the generator added.

EXAMPLE 23

Spray-Dried Instant Coffee Flavor Enhancement using 1,2-di[(1'-Ethoxy)Ethoxy]Propane A control coffee sample was made dissolving 3.52 g. of instant coffee (Maxwell House Instant, General Foods) in eight ounces of boiling water. The coffee beverage had a pH of 4.8. Another sample was made up in the same way but in addition 0.005 g. of the same spray-dried generator used in Example 8 was added. Four out of five professional flavorists found the coffee with the added generator to have what was described as either an improved or fresher aroma and taste.

EXAMPLE 24

Salad Dressing made from a Dry Mix Flavor Enhancement using 1,2-di[(1'-Ethoxy)Ethoxy)]Propane A mayonnaise-flavored salad dressing mix was formulated in the following manner:

| | |
|---|---|
| Modified Starch (Maltrin M-10 - Grain Processing Co.) | 50.2 |
| Sucrose (fine granulated) | 31.9 |
| Salt | 12.3 |
| Cellulose Gum Type 7H3SXF (Hercules) | 3.2 |
| Mayonnaise Flavor | 2.1 |
| Parsley Flakes (dehydrated) | 0.14 |
| Onion Powder | 0.10 |
| Ground White Pepper | 0.50 |

A 20-gram portion of the above mixture was combined with 29.6 g. of water and 14.6 g. of vinegar. The pH of this mixture was 3.3. The mixture was combined with 49.2 g. of oil and shaken until blended. The title generator compound was added at a ratio of 0.02 and 0.05 g. per 100 g. of salad dressing in two different comparison samples. When compared to a control to which no acetal had been added, an improvement in taste of the dressing was noted by a group of professional flavorists.

EXAMPLE 25

Cherry Hard Candy Flavor Enhancement using 1,2-di[(1'-Ethoxy)Ethoxy]Propane

A hard candy base was made by combining 225 g. of water, 350 g. of corn syrup, 700 g. of sugar and heating the mixture to 135° C. Upon reaching this temperature, the melt was poured onto a slab and flavor was mixed in. A control was made up by adding 1.25% citric acid, 0.375% Cherry Flavor, and four drops of a 10% solution of Red #40.

A test sample was formulated as described above for the control, but in addition $1.25 \times 10^{-2}\%$ of the title generator was added in with the flavor oil. The candy with the acetal was found by a group of professional flavorists to have a stronger, fresher, improved flavor when compared to the control.

EXAMPLE 26

Orange Gum Flavor Enhancement using 1,2-di[(1'-Ethoxy)Ethoxy]Propane

Chewing gum base was formulated as follows: chicle (28.5 g.) was melted in a double boiler, 25 g. of corn syrup was stirred in for five minutes and the heat turned off. One-half of a 45.5 g. portion of powdered sugar was mixed in, followed by 1 g. of glycerine and then the remainder of the powdered sugar.

A control sample of gum was formulated by melting the gum base in a double boiler and adding 0.5% of Orange Flavor, two drops of a 10% solution of Yellow #6, and 0.125% citric acid. The enhanced gum sample was made as above except that in addition 0.0625% of the title generator compound was added. A group of professional flavorists found the gum containing the acetaldehyde generator to have a fresher, more natural, improved orange flavor.

EXAMPLE 27

Tomato Sauce Flavor Enhancement using 1,2-di[(1'-Ethoxy)Ethoxy]Propane

To 200 g. of Hunt's (Hunt-Wesson Foods) tomato sauce, which had a pH of 4.2, was added $4.3 \times 10^{-3}\%$ of 1,2-di[(1'-ethoxy)ethoxy]propane. The sauce was heated for two minutes to simmer and compared to a similarly heated control to which no generator compound had been added. When the two samples were compared by a group of professional flavorists, the generator-enhanced sample was found to have a fresher taste effect.

EXAMPLE 28

Hot Cocoa Flavor Enhancement using 1,2-di[(1'-Ethoxy)Ethoxy]Propane

A one-ounce pack of Carnation Instant Hot Cocoa mix was dissolved in eight ounces of boiling water. A second pack, to which $1.2 \times 10^{-3}$ g. of the title acetal was added, was dissolved in a similar manner. The pH was 6.5. The beverage to which the acetal was added had a richer chocolate flavor.

EXAMPLE 29

Instant Tomato Soup Flavor Enhancement using 1,2-di[(1'-Ethoxy)Ethoxy]Propane

A 19.2 g. pack of Nestle's Souptime Tomato Soup was combined with six ounces of boiling water. The pH was 4.3. A second soup pack, to which $9 \times 10^{-4}$ g. of the title acetal was added, was compared to the first and found by the large majority of those testing it (seven out of nine) to be preferred, having an improved tomato aroma and taste.

EXAMPLE 30

Flavor Enhancement of Chocolate Pudding using 1,2-di[(1'-Ethoxy)Ethoxy]Propane

A package of My-T-Fine chocolate pudding and pie filling was combined with two cups of milk and the mixture cooked over medium heat with stirring until boiling started and the mixture was poured into cups to set. A sample was also made up with $4.4 \times 10^{-4}\%$ of the title acetal. The pH was 6.7. The pudding to which acetal had been added possessed an improved chocolate flavor.

EXAMPLE 31

Flavor Enhancement of Canned Orange Drink using 1,2-di[(1'-Ethoxy)Ethoxy]Propane A can of Hi-C canned orange drink (pH 3.3) was split into three portions and $1.7 \times 10^{-4}\%$ of the title acetal was added to one portion, while $4.4 \times 10^{-4}\%$ was added to another. Ten out of twelve tasters preferred one or the other of the acetal-fortified beverages.

EXAMPLE 32

Flavor Enhancement of Canned Cherry Drink using 1,2-di[(1'-Ethoxy)Ethoxy]Propane A can of Hi-C canned cherry drink was split into three portions and $1.7 \times 10^{-4}\%$ of the title acetal was added to one portion, while $4.4 \times 10^{-4}\%$ was added to another. Seven out of ten tasters found either one of the acetal-fortified beverages to be preferred.

EXAMPLE 33

Flavor Enhancement of Salad Dressing using 1,2-di[(1'-Ethoxy)Ethoxy]Propane

Combined one quarter cup of vinegar, two tablespoons of water, a one-ounce package of Good Seasons Italian Dressing and mixed well. Next, two-thirds of a cup of salad oil was added and the mixture was shaken again. To one portion of the salad dressing was added $1.3 \times 10^{-4}\%$ of the title acetal. Eight out of twelve tasters preferred the acetal-fortified dressing, the general opinion being that it had a more pronounced and well-balanced flavor.

EXAMPLE 34

Flavor Enhancement of Canned Orange Drink using 1,2-di[(1'-Ethoxy)Ethoxy]Propane A can of orange Hawaiian Punch was divided into three portions and $1.7 \times 10^{-4}\%$ of the title acetal was added to one portion, while $4.4 \times 10^{-4}\%$ was added to another. Eleven of thirteen tasters found either one or the other of the generator-treated portions to be preferred.

EXAMPLE 35

Flavor Enhancement of Canned Cherry Drink using 1,2-di[(1'-Ethoxy)Ethoxy]Propane A can of Cherry Hawaiian Punch was divided into three portions and $1.7 \times 10^{-4}\%$ of the title acetal was added to one portion, while $4.4 \times 10^{-4}\%$ was added to another. Seven of eleven tasters preferred either one or the other of the acetal-fortified beverages.

EXAMPLE 36

Dill Pickle Flavor Enhancement using 1,2-di[(1'-Ethoxy)Ethoxy]Propane

Chopped dill pickles with packing juice were split into three portions and $1.7 \times 10^{-4}\%$ of the title acetal was added to one portion, while $4.4 \times 10^{-4}\%$ was added to another. Five tasters unanimously found the acetal-fortified pickles to be preferred over the control. The spice flavor of the pickles was enhanced.

EXAMPLE 37

Flavor Enhancement of Raspberry Beverage Using 1,2-[(1'-Ethoxy)Ethoxy]Propane

A raspberry flavored beverage was prepared using the following formulation:

| Ingredient | Weight in Grams |
| --- | --- |
| Sugar | 96.68 |
| Citric acid | 2.19 |
| Carboxymethyl cellulose (D.S. 0.9) | 0.75 |
| Artifical raspberry flavor | 0.14 |
| Red #40 | 0.11 |
| Blue #1 (1% in lactose) | 0.08 |
| Ascorbic acid | 0.05 |

A control beverage was made by dissolving 50 g. of the powder mix in 16 ounces of water. A second beverage was made in a similar manner with the exception that 0.1 g. of a 10% solution of 1,2-[(1'-ethoxy)propoxy]propane in ethanol was also added. The propionaldehyde freshness note generated from the acetal was readily noted by a group of flavorists.

EXAMPLE 38

Flavor Enhancement of Orange Beverage Using 1,2-Di[(1'-Butoxy)Ethoxy]Propane

An orange flavored beverage was prepared using the following formulation:

| Ingredient | Weight in Grams |
| --- | --- |
| Sugar | 86.53 |
| Citric acid | 5.00 |
| Ascorbic acid | 1.00 |
| Potassium citrate | 2.00 |
| Carboxymethyl cellulose (D.S. 0.7) | 0.16 |
| Gum arabic type CF-Fd | 1.30 |
| Clouding agent | 2.50 |
| Yellow #5 (10% in lactose) | 0.40 |
| Yellow #6 (1% in lactose) | 0.80 |
| Artificial orange flavor | 0.31 |

A control beverage was made by dissolving 82.5 g. of the above mixture in 16 ounces of water. A second beverage was made in a similar manner with the exception that 0.16 g. of a 10% solution in ethanol of the title acetal was also added. A fresher orange effect was seen with the acetal boosted flavor versus the control.

EXAMPLE 39

Orange Beverage Flavor Enhancement Using 1-Benzyloxy-1-n-Butoxy Ethane

A control orange beverage was formulated as described in Example 38. A second beverage was made in a similar manner except that 0.26 g. of ten percent solution of the title acetal in ethanol was also added. The acetal fortified beverage was found to have a fresher, juicy-orange effect when compared to the control.

EXAMPLE 40

Orange Beverage Flavor Enhancement Using 1-Ethoxyethyl 2-(1''-Ethoxyethoxy)Propionate A control orange beverage was formulated as described in Example 38. A second beverage was made in a similar manner except that 0.15 g. of a ten percent solution of the title acetal in ethanol was also added. The acetal fortified beverage had a fresh-squeezed juice taste when compared to the control.

EXAMPLE 41

Orange Beverage Flavor Enhancement Using Diethyl 2-[(1'-Ethoxy)Ethoxy]Succinate

A control orange beverage was formulated as described in Example 38. A second beverage was made in a similar manner except that 0.39 g. of a ten percent solution of the title acetal in ethanol was also added. A fresh juice effect (acetaldehyde note) was observed with the acetal fortified beverage when compared to the control.

EXAMPLE 42

Orange Beverage Flavor Enhancement Using Ethyl 2-[(1'-Methoxy)n-Decyloxy]Propionate A control beverage was made by adding 0.2 ml. of a 1% solution of Valencia orange oil in ethanol to a mixture of 17 ml. of citric syrup brought to 100 ml. with water. A second beverage was made in the same manner except 7% of the title acetal was mixed with the orange oil prior to dilution in ethanol. The decanal generator was found to enhance the flavor of fortified beverage and give it a taste closer to that of a folded oil, enhancing the c-10 note.

What I claim and desire to protect by Letters Patent is:

1. An edible composition comprising a foodstuff and an effective amount of an aldehyde generating linear acetal compound to deliver rapidly a flavor and/or freshness impact-enhancing amount of aldehyde to be present in the foodstuff during consumption of the foodstuff of the general formula:

wherein R is a 3 to 6 carbon straight chain multivalent hydrocarbon; n is an integer from 2 to 6; $R_1$ is a hydrocarbon radical having from 1 to 14 carbons selected from the group consisting of straight or branched chain alkyl and phenyl radicals; and $R_2$ is an aliphatic or cycloaliphatic radical of 1 to 6 carbon atoms, a benzyl radical or an aliphatic acyl group.

2. The composition of claim 1 wherein said compound is 1,2,3-tris[(1'-ethoxy)ethoxy] propane.

3. The composition of claim 1 wherein said compound is 1,2,3,4,5,6-hexa[(1'-ethoxy)ethoxy] hexane.

4. The composition of claim 1 wherein said compound is 1,2-di[(1'-ethoxy)propoxy] propane.

5. The composition of claim 1 wherein said compound is 1,2-di[(1'-butoxy)ethoxy] propane.

6. The composition of claim 1 wherein said foodstuff is a beverage powder.

7. The composition of claim 1 wherein said foodstuff is a dessert mix.

8. The composition of claim 1 wherein said foodstuff is a confectionery.

9. The composition of claim 8 wherein the effective amount of said compound comprises from 5 to 1000 ppm of said composition.

10. The composition of claim 1 wherein said composition is a dry powder.

11. The composition of claim 1 wherein said compound is encapsulated in a spray dried matrix.

12. The composition of claim 1 wherein the rapid delivery of the flavor and/or freshness impact-enhancing amount of aldehyde to the foodstuff is based on the foodstuff having a pH of 3 at a temperature of about 23° C. and a degree of hydrolysis of the aldehyde-generating compound being greater than 50% in about 10 minutes.

13. The composition of claim 12 wherein said compound and its hydrolysis products do not interfere with the desired flavor.

14. An edible composition comprising a foodstuff and an effective amount of an aldehyde generating linear acetal compound for rapidly delivering a flavor and/or freshness impact-enhancing amount of aldehyde to be present in the foodstuff during consumption of the foodstuff of 1,2-di[(1'-ethoxy)ethoxy] propane.

15. A method of forming an edible foodstuff with flavor and/or freshness enhanced comprising
mixing together to form a composition a foodstuff and an effective amount of an aldehyde generating linear acetal compound for rapidly delivering a flavor and/or freshness impact-enhancing amount of aldehyde to be present in the foodstuff during consumption of the foodstuff, said compound having the general formula:

wherein R is a 3 to 6 carbon straight chain multivalent hydrocarbon, n is an integer from 2 to 6, $R_1$ is a hydrocarbon radical having from 1 to 14 carbons selected from the group consisting of straight or branched chain alkyl and phenyl radicals, and $R_2$ is an aliphatic or cycloaliphatic radical of 1 to 6 carbon atoms, a benzyl radical or an aliphatic acyl group.

16. The method of claim 15 wherein said compound is 1,2,3-tris[(1'-ethoxy)ethoxy] propane.

17. The method of claim 15 wherein said compound is 1,2-di[(1'-ethoxy)propoxy] propane.

18. The method of claim 15 wherein said compound is 1,2-di[(1'-butoxy)ethoxy] propane.

19. The method of claim 15 wherein said compound is 1,2,3,4,5,6-hexa[(1'-ethoxy)ethoxy] hexane.

20. The method of claim 15 wherein said composition is a dry powder.

21. The method of claim 15 wherein said compound is encapsulated in a solid matrix by spray drying.

22. The method of claim 15 further comprising admixing a flavor with said foodstuff and said compound, and wherein the rapid delivery of the flavor and/or freshness impact-enhancing amount of aldehyde to the foodstuff is based on the foodstuff having a pH of 3 at a temperature of about 23° C. and degree of hydrolysis of the aldehyde-generating compound being greater than 50% in about 10 minutes.

23. The method of claim 22 wherein said compound and its hydrolysis products do not interfere with the desired flavor.

24. A method of forming an edible foodstuff with flavor and/or freshness enhanced comprising mixing together to form a composition a foodstuff and an effective amount of an aldehyde generating linear acetal compound for rapidly delivering a flavor and/or freshness impact-enhancing amount of aldehyde to be present in the foodstuff during consumption of the foodstuff of 1,2-di[(1'-ethoxy)ethoxy] propane.

* * * * *